United States Patent
Carlson et al.

(10) Patent No.: US 7,458,248 B2
(45) Date of Patent: Dec. 2, 2008

(54) METHOD AND APPARATUS TO DETECT GENUINE OR HOAX CONTAMINANTS

(75) Inventors: Micah A. Carlson, Baltimore, MD (US); Adam K. Arabian, Louisville, KY (US); Michael P. McLoughlin, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/501,320

(22) PCT Filed: Apr. 15, 2003

(86) PCT No.: PCT/US03/11740

§ 371 (c)(1),
(2), (4) Date: Jul. 13, 2004

(87) PCT Pub. No.: WO03/089909

PCT Pub. Date: Oct. 30, 2003

(65) Prior Publication Data

US 2004/0255644 A1 Dec. 23, 2004

Related U.S. Application Data

(60) Provisional application No. 60/373,003, filed on Apr. 16, 2002.

(51) Int. Cl.
G01N 1/20 (2006.01)
G01N 1/22 (2006.01)

(52) U.S. Cl. .................. 73/31.07; 73/31.03; 73/863.21; 73/863.23; 340/632; 435/287.1

(58) Field of Classification Search .................. 73/23.2, 73/28.01, 31.01–31.04, 31.07, 863.21, 863.22, 73/863.23, 863.71, 864.33, 1.03; 435/287.1; 340/540, 632

See application file for complete search history.

(56) References Cited

U.S. PATENT DOCUMENTS

| 4,275,875 | A | * | 6/1981 | Akers ............................ 271/5 |
| 4,718,268 | A | * | 1/1988 | Reid et al. .................. 73/19.01 |
| 5,859,362 | A |   | 1/1999 | Neudorfl et al. .............. 73/23.2 |
| 6,413,424 | B1 | * | 7/2002 | Shelby .................. 210/321.74 |
| 6,684,682 | B2 | * | 2/2004 | Stemmle et al. .............. 73/23.2 |
| 2002/0124664 | A1 |   | 9/2002 | Call et al. ................. 73/863.22 |
| 2002/0126008 | A1 | * | 9/2002 | Lopez et al. ................. 340/540 |
| 2003/0119175 | A1 |   | 6/2003 | Stradley et al. .......... 435/287.1 |
| 2003/0136203 | A1 | * | 7/2003 | Yoon ....................... 73/864.33 |
| 2004/0020264 | A1 | * | 2/2004 | Megerle .................... 73/19.01 |

* cited by examiner

Primary Examiner—David A. Rogers
(74) Attorney, Agent, or Firm—Francis A. Cooch (57) ABSTRACT

A system (100) and method for detecting contaminants in parcels or other mailings (110). The contaminants, either genuine or hoax, are detected using the system (100) that includes a jogger (140) that shakes the parcels or other mailings (110). The system (100) further comprises a particle sampler (170) that analyzes the air flow created over the parcels (110) while the parcels are shaken. The system (100) and method preferable includes a parcel opening cutter (120) and a ram (148) for compressing during the shaking of the parcels. The air flow is sampled in order to detect whether or not a plurality of opened parcels is suspected of including contaminants such as biological threat material.

3 Claims, 6 Drawing Sheets

METHOD AND APPARATUS TO DETECT GENUINE OR HOAX CONTAMINANTS

CROSS-REFERENCE TO RELATED APPLICATIONS

This application claims priority to Provisional Application Ser. No. 60/373,003 entitled "DETECTION OF GENUINE AND HOAX BIOLOGICAL AND NON-BIOLOGICAL CONTAMINANTS ON VARIOUS MEDIA", filed on Apr. 16, 2002, the contents of which are incorporated herein by reference.

STATEMENT OF GOVERNMENTAL INTEREST

This invention was made with Government support under Contract No. N00024-98-D-8124 awarded by the Department of the Navy. The Government has certain rights in this invention.

BACKGROUND OF THE INVENTION

1. Field of the Invention

The present invention generally relates to systems for handling and screening parcels to detect contamination thereof, and applications thereof.

2. Description of the Related Art

Numerous parcel handling systems have been developed and are in use. The United States Postal Service (USPS) utilizes such systems to handle the enormous quantity of parcels that are delivered each day by the USPS. A notable feature, and an inherent disadvantage, of the USPS system is that the sender of a parcel can remain anonymous.

Following the terrorist attacks of Sep. 11, 2001, the U.S. mail was utilized to propagate bioterrorist attacks upon high level governmental representatives and important members of the media. A number of similar hoax attacks have followed and continue to this day. The ability of users of the USPS to remain anonymous has thwarted law enforcement efforts to apprehend the bioterrorist(s).

The need for an apparatus and method for sanitizing parcels that may contain particles of biological contaminant, i.e. anthrax, non-biological contaminant, or other particulate matter or powders, that have the ability to become airborne, has become apparent. The overwhelming volume of parcels handled by the USPS and other entities, however, has made it impossible to sanitize every parcel delivered. Nonetheless, following the bioterrorist attacks, the USPS began a campaign of irradiating parcels sent to persons and organization that are likely terrorist targets.

Irradiation, however, is recognized as being an inadequate long-term defense. Aside from entailing an unduly long time to irradiate parcels, the double digit kilogray doses that are needed to kill anthrax spores makes paper contained within the parcels brittle and smelly, and is fatal to film, magnetic media, electronic devices and prescription drugs that are in the parcels that pass through the irradiating machines. The irradiation has also led to reports of sickness of the workers at mail processing facilities.

A further shortcoming is that irradiation simply kills the contaminant, and does nothing to identify contaminated parcels, such as envelopes and boxes. Identification of contaminated parcels is an essential threshold requirement for law enforcement to identify and apprehend the terrorists.

Other techniques that can be used to sanitize suspect parcels include the use of penetrative gamma rays or chemical sterilization, such as by use of chlorine dioxide gas. Each has its drawbacks. Use of penetrative gamma rays raises concerns of housing radioactive gamma sources such as cobalt-60, and chlorine dioxide gas requires lengthy exposure time for adequate penetration of the parcels.

The techniques and apparatus known in the art either require individual treatment of the parcels or require prolonged exposure to the sterilization method.

While known techniques can sanitize parcels, the known techniques fail to screen suspect parcels and cause an unacceptable processing delay of such parcels. Further, the known techniques fail to identify suspect parcels, as necessary to advance the efforts of authorities to apprehend the terrorists and hoax perpetrators.

SUMMARY OF THE INVENTION

The present invention provides the advantage of allowing real-time screening of parcels for detection of possible contaminants. The screening can be performed either prior to or following irradiation or other parcel sterilization processes.

The present invention can be utilized to winnow the number of parcels that must be subjected to irradiation or other sterilization means, thereby accelerating the processing of the parcels.

Further, the present invention allows for timely screening of previously irradiated parcels, wherein such additional screening is useful in detecting parcels containing contaminant residue or powder or other hoax threat.

In accordance with one embodiment of the present invention, an apparatus that allows for rapid screening and identification of parcels likely to contain biological or non-biological contaminants is provided comprising a jogger for shaking a plurality of parcels, an air duct for channeling an air flow over the plurality of parcels in the jogger, and a particulate sampler for analyzing the air flow to detect whether the plurality of opened parcels is likely to include contaminants.

In accordance with another embodiment of the present invention, an apparatus that allows for rapid screening and identification of parcels likely to contain biological or non-biological contaminants is provided comprising a cutter for opening each parcel, a jogger for shaking the opened parcels, an air duct for channeling an air flow obtained when the jogger shakes the parcels, and a particulate sampler connected by the air duct to the jogger, wherein the particulate sampler analyzes the air flow to detect whether the plurality of parcels is likely to include contaminants.

A method is also provided for rapid screening of parcels to identify parcels likely to contain particles of biological or non-biological contaminants, comprising the steps of shaking the parcels, creating an air flow over the parcels as the parcels are shaken, and analyzing the air flow to detect whether the parcels are likely to include contaminants.

BRIEF DESCRIPTION OF THE DRAWINGS

The following detailed description provides a better understanding of the invention as well as other objects and further features thereof, in which reference is made to the accompanying drawings, wherein:

FIG. 5b is a close-up view of a portion of the apparatus of FIG. 5a;

FIG. 6b is another perspective view of the first class mail jogger of FIG. 6a.

DETAILED DESCRIPTION OF THE INVENTION

The following detailed description of the invention will be made in reference to the accompanying drawings. In describing the invention, explanation of related functions or constructions known in the art are omitted for the sake of clearness in understanding the concept of the invention, to avoid obscuring the invention with unnecessary detail.

Figure 1:
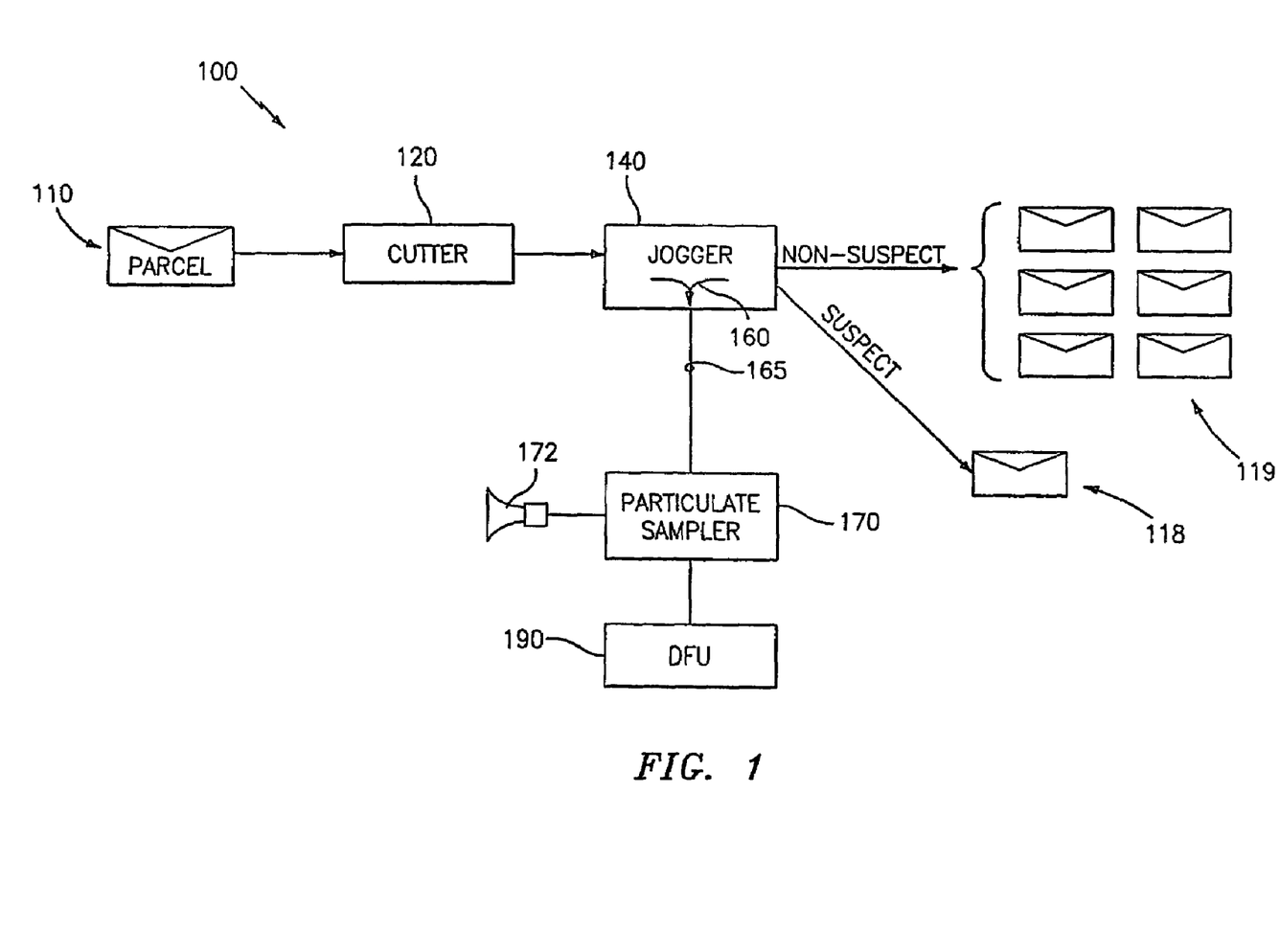
FIG. 1 is a block diagram showing a preferred embodiment of the present invention.

FIG. 1 is a block diagram showing the various components of the apparatus 100. The parcels 110, a/k/a media, that are to be screened include those which have an enclosed portion as well as parcels which lack an enclosed portion. Examples of parcels 110 include, but are not limited to, postcards, letters, envelopes, magazines and other flats (i.e. parcels containing unfolded material), as well as boxes. The parcels 110, other than postcards and similar media that lack an enclosed portion, are, in a preferred embodiment, first opened by a cutter 120.

After the cutter 120 opens the parcel 110, the parcel 110 is loaded into a jogger 140, which shakes the parcel 110, causing release of any particles contained within or on the parcel 110.

An air duct 165 connects with the jogger 140 and diverts an airflow 160 over the shaken parcel 110 to a particulate sampler 170, which notifies the operator of the apparatus 100, via an indicator alarm 172, when the air flow 160 contains either a high concentration of particles or particles with suspect characteristics. The air flow 160 over the parcels 110 in the jogger 140 is preferably created by a particulate concentrator 190, which is located downstream from the particulate sampler 170, drawing a vacuum on air duct 165, and may alternatively be created by pressurizing the jogger 140.

Any parcels 110 that are in the jogger 140 when the indicator alarm 172 sounds are identified as being suspect parcels 118. In the event that an alarm is not received from indicator alarm 172, the parcels 110 in the jogger 140 are determined to be non-suspect parcels 119.

Suspect parcels 118 are isolated for more detailed confirmatory analysis, such as PCR (polymerase chain reaction) analysis. This confirmatory analysis is performed separately and will not cause delay of the inline, real-time screening process and method of the present invention.

Figure 2:
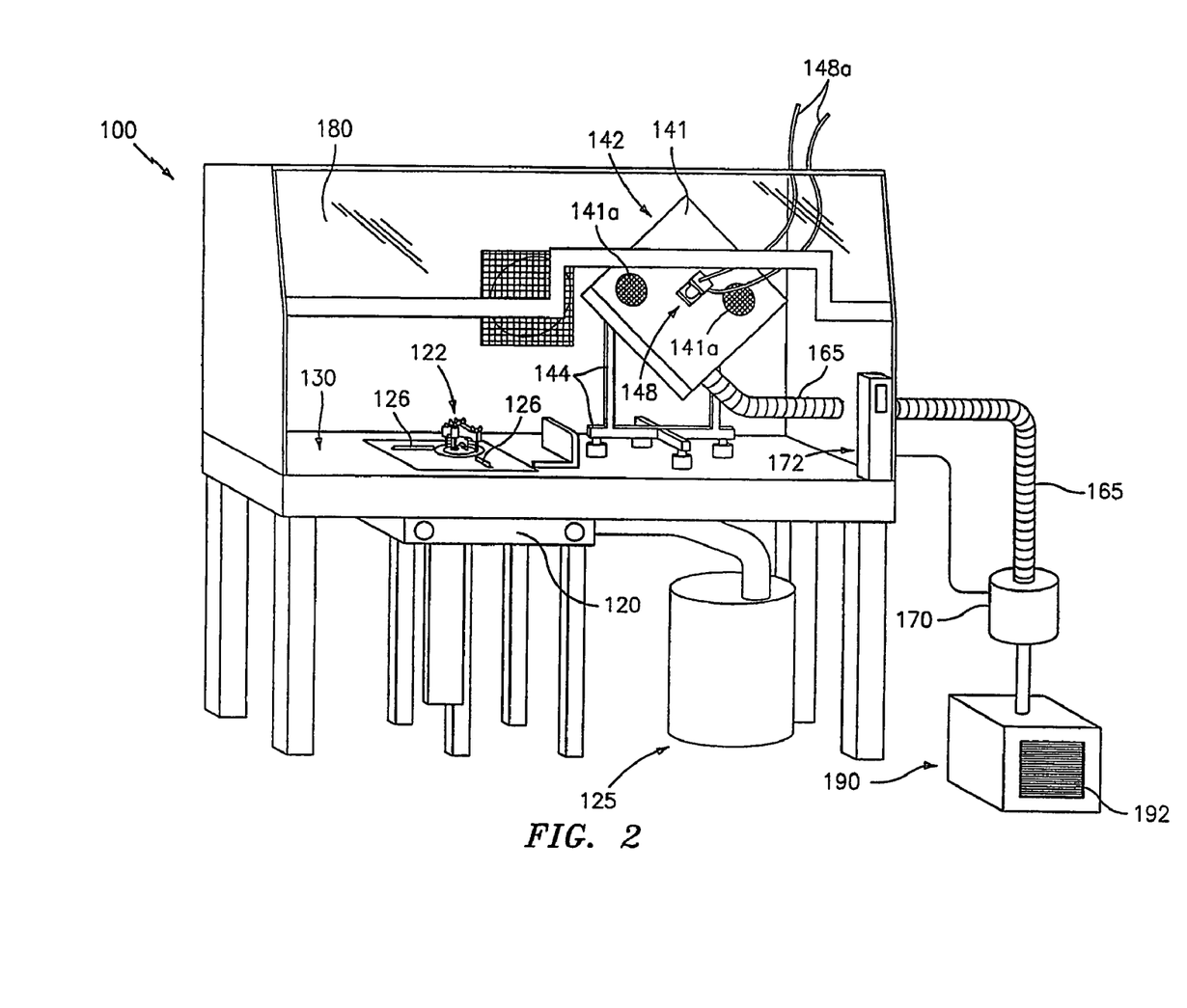
FIG. 2 is a front perspective view of one embodiment of the apparatus 100 of the present invention.

The particulate concentrator 190 is equipped with a screen 192, as shown in FIG. 2. The screen 192 is preferably constructed in manner similar to that utilized to construct a dry-type high efficiency particulate air (HEPA) filter. The particulate concentrator 190 captures, i.e. collects or concentrates, aerosolized particles which are ejected from the parcel 110.

Each screen 192 is preferably provided with a unique identifier and is analyzed at periodic intervals, thereby providing a second-check of the accuracy of the screening provided by the particulate sampler 170. To facilitate the second-check capability of the analysis performed by the particulate sampler 170, parcels 110 which are found to be non-suspect parcels 119 are quarantined in groups corresponding to a specific screen 192 that was in place at the time the non-suspect parcels 119 were screened. If the periodic analysis of the screen 192 detects biological or non-biological contaminants during a time frame when none of the parcels 110 were identified as being suspect parcels 118, the entire quarantined group can either be re-screened or submitted for further testing.

It will be recognized by those of skill in the art that the function of the dry-type filter of screens 192 which are depicted for illustrative purposes in FIG. 2 can be performed by other types of confirmatory analysis systems, such as a liquid or solid sampler units which collect aerosolized particles, as well as by concentrator units. Also, in certain embodiments known in the art, particulate collectors units can also serve to act as concentrators. Accordingly, "particulate concentrator" is used herein to mean concentrators, collectors and units that acts as both concentrators and collectors.

The particulate concentrator 190 is arranged to capture respirable particles, which present research indicates are generally those particles between about 0.3 and 10 microns in size.

FIG. 2 is a front perspective view of one embodiment of the apparatus 100 of the present invention which includes a cutter 120, a flats jogger 142, an air duct 165, a particulate sampler 170, an indicator alarm 172 and a particulate concentrator 190.

The cutter 120, which is preferably integrated with the apparatus 100, is a conventional letter opener that is preferably adapted to operate as a corner cutter. The cutter 120 that is preferably included in the apparatus 100 of the present invention comprises a conventional cutter that has been modified to prolong blade life by reducing the length of the slice made to each parcel 110. Accordingly, the cutter 120 of the present invention slices open and removes one corner of each parcel 110. The cutter 120 includes a blade/slicer 122 operationally exposed on top of the cutter 120. Cutter guides 126 are provided to allow the operator to readily position the parcel 110 in the cutter.

Removal of the corner of the parcel 110 creates a defined path for egress of any contaminants within the parcel 110. Further, by slicing open only the corner, rather than slicing open an entire edge of the parcel 110, the integrity of the original seal of the parcel 110 is maintained. This provides assurance to the recipient that the contents of parcels 110 which are of a sensitive nature have not been compromised by the screening process. Further, the unique corner cut left by the cutter 120 of the present invention serves as an identifiable indication that the parcel 110 has been screened for contaminants.

As shown in FIG. 2, the cutter 120 can be connected to a corner collector 125 that vacuums away corners cut from the parcels 110, keeping the work table 130 of the apparatus clear of cutting debris.

In an alternative embodiment, the cutter 120 is modified to punch, rather than slice or cut, an opening in parcel 110. Such an embodiment is preferably used to screen parcels 110 such as boxes.

The present invention uses a modified conventional table top paper jogger 140. Conventional paper joggers are utilized in mailroom and mail processing facilities to shake groups of parcels 110 into a uniform alignment, creating a stack of parcels aligned along a common edge. Conventional joggers include a frame 144 and an oscillating motor (not shown) which connects the frame 144 and a bin 141. When activated, the oscillating motor jogs, i.e. shakes and agitates, the parcels 110 that are loaded in the bin 141 of the jogger 140. The shaking liberates particles contained in and on the parcel 110.

As shown in Table 1 (percentage of amount liberated), the jogger 140 was successful in liberating contaminants when tested with various hoax materials and various letter preparation methods (e.g. loose folded, etc.) when the parcels 110 were shaken.

TABLE 1

|  | Hoax material 1 | Hoax material 2 | Hoax material 3 |
|---|---|---|---|
| First preparation method | 8% | 15% | 17% |
| Second preparation method | 13% | 25% | N/a |
| Third preparation method | 10% | 16% | N/a |
| Partial opening created | — | 50% | — |

The jogger shown in FIG. 2 is a flats jogger 142, which is essentially a conventional jogger that has been modified to include the air duct 165, air inlets 141a, and a ram 148.

The ram 148 is a further preferred feature of the present invention. The ram 148 compresses the parcel 110 that is loaded in the bin 141, preferably at the same time that the parcel 110 is being shaken by the jogger 142. The compressing further assists in releasing any particles contained within the parcel 110. The ram 148 is preferably pneumatically actuated via pneumatic lines 148a from a controller (not shown).

The air duct 165 shown in FIG. 2 channels the air flow 160 toward the particulate sampler 170, which samples the particles in the air flow 160. The particles in the air flow 160 are sampled in a real-time manner to provide an essentially immediate indication of whether the parcels 110 in bin 141 are suspected of being contaminated with genuine or hoax biological or non-biological contaminants.

The particulate sampler 170 can utilize one or a combination of detection methods, including absolute particle count detection, particle size discriminatory detection, particle fluorescence detection and/or particle fluorescence coupled with size detection. The particulate sampler 170 preferably utilizes a particle counter, such as that manufactured by Climet Instruments Company and sold under the CLiMET® trademark, to perform the detection of suspect parcels 118.

Initial testing indicated that certain types of parcels 110 produce high background particle counts. For example, post cards were found to produce a particle distribution that is highly concentrated in the 1 to 5 micron size range. Such high background and other obscurant aerosols can produce unacceptable false alarms or mask the finding of a contaminated parcel. Such high background particle counts can be overcome by physically separating and processing in separate batches certain types of parcels 110, e.g. postcards, known to have high background levels.

Figure 3:
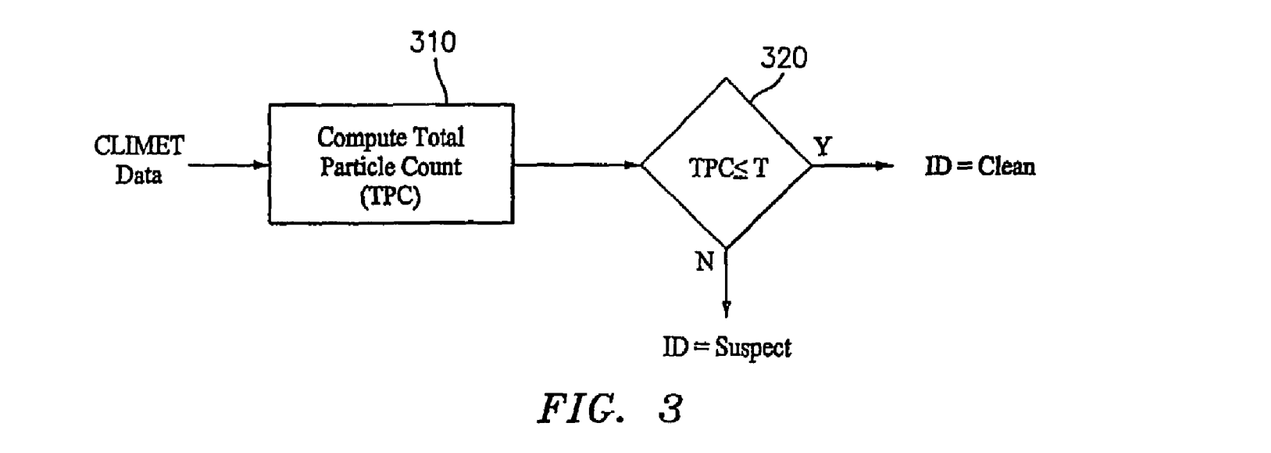
FIG. 3 is a flowchart of a process for performing a total particulate count threshold detection.
Figure 4:
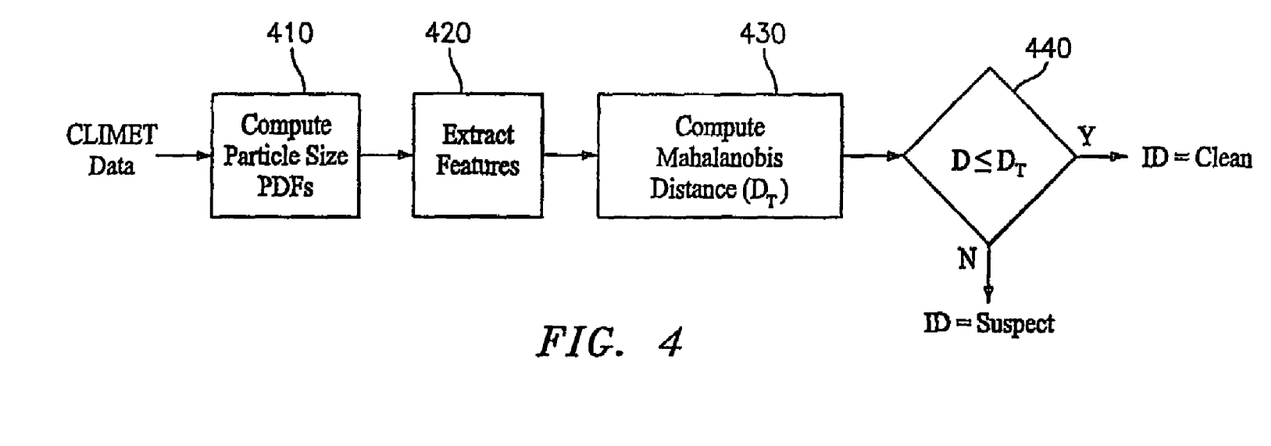
FIG. 4 is a flowchart for performing detection utilizing a Multivariate Gaussian classifier.

Predetermined characteristic signatures of contaminants and hoax particles can also be utilized by the particulate sampler 170. FIG. 3 depicts a process for a performing threshold detection by comparing (in step 320) a total particle count (TPC) computed from the CLiMET data (step 310) with an acceptable threshold (T). Alternatively, or additionally, as shown in the flowchart of FIG. 4, an MVG (Multivariate Gaussian) classifier can analyze the CLiMET data. In step 410 the size of the particles in the air flow 160 is computed and the features of the particles are extracted (step 420). A Mahalanobis Distance ($D_T$) is then computed (step 430). In step 440, the computed $D_T$ is compared to a previously computed Mahalanobis Distance (D) for clean, non-suspect parcels 119. A determination of whether the parcel 110 is a suspect parcel 118 or a non-suspect parcel 119 is then made.

Figure 5A:
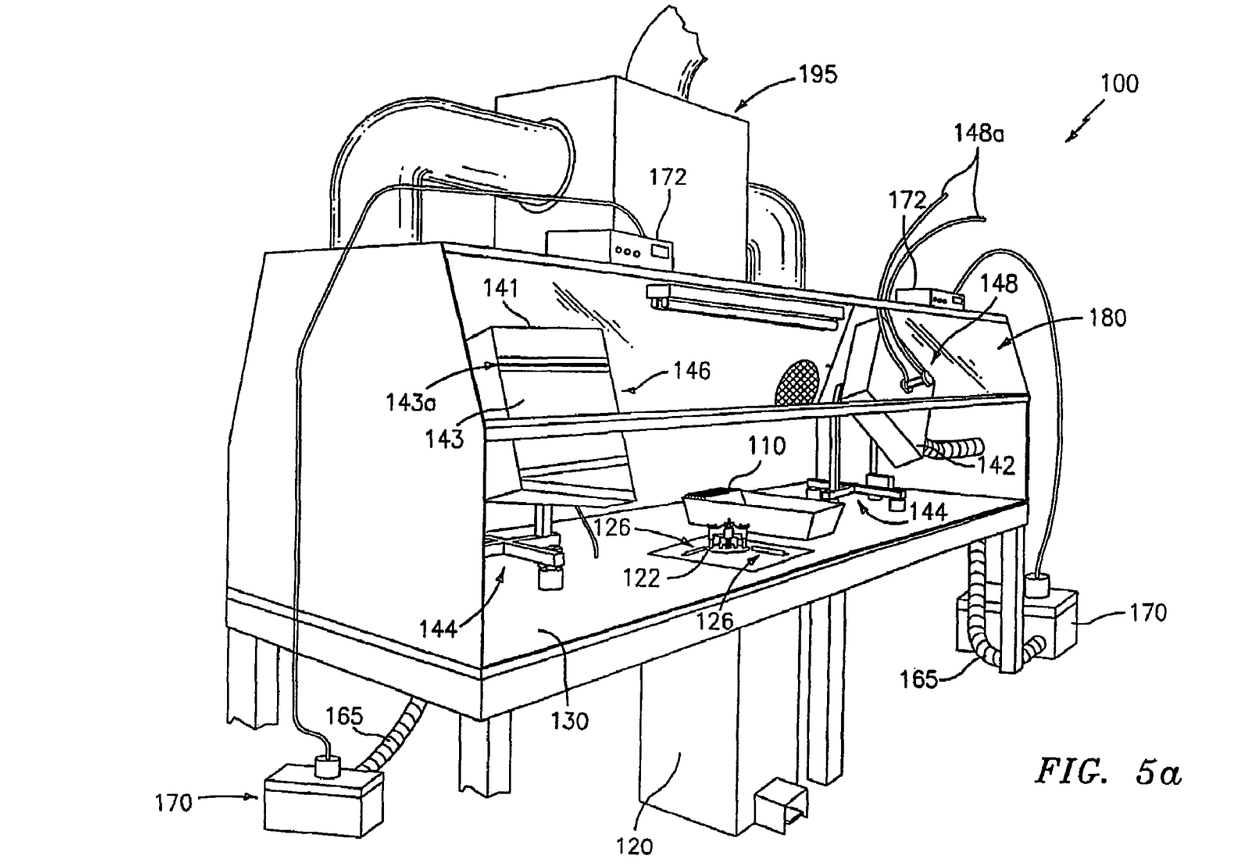
FIG. 5a is a perspective view of the apparatus equipped with both flats and first class mail joggers in accordance with the present invention.

FIG. 5a is a perspective view of an embodiment of the apparatus 100 equipped with a flats jogger 142 and a first class mail jogger 146 located on opposite sides of the cutter 120. The apparatus 100 of FIG. 5a has separate particulate scanners 170 for each jogger. The close-up perspective view provided in FIG. 5b provides a more detailed view of the particulate scanner 170 that functions with the first class mail jogger 146 and other components of the apparatus 100.

Figure 5B:
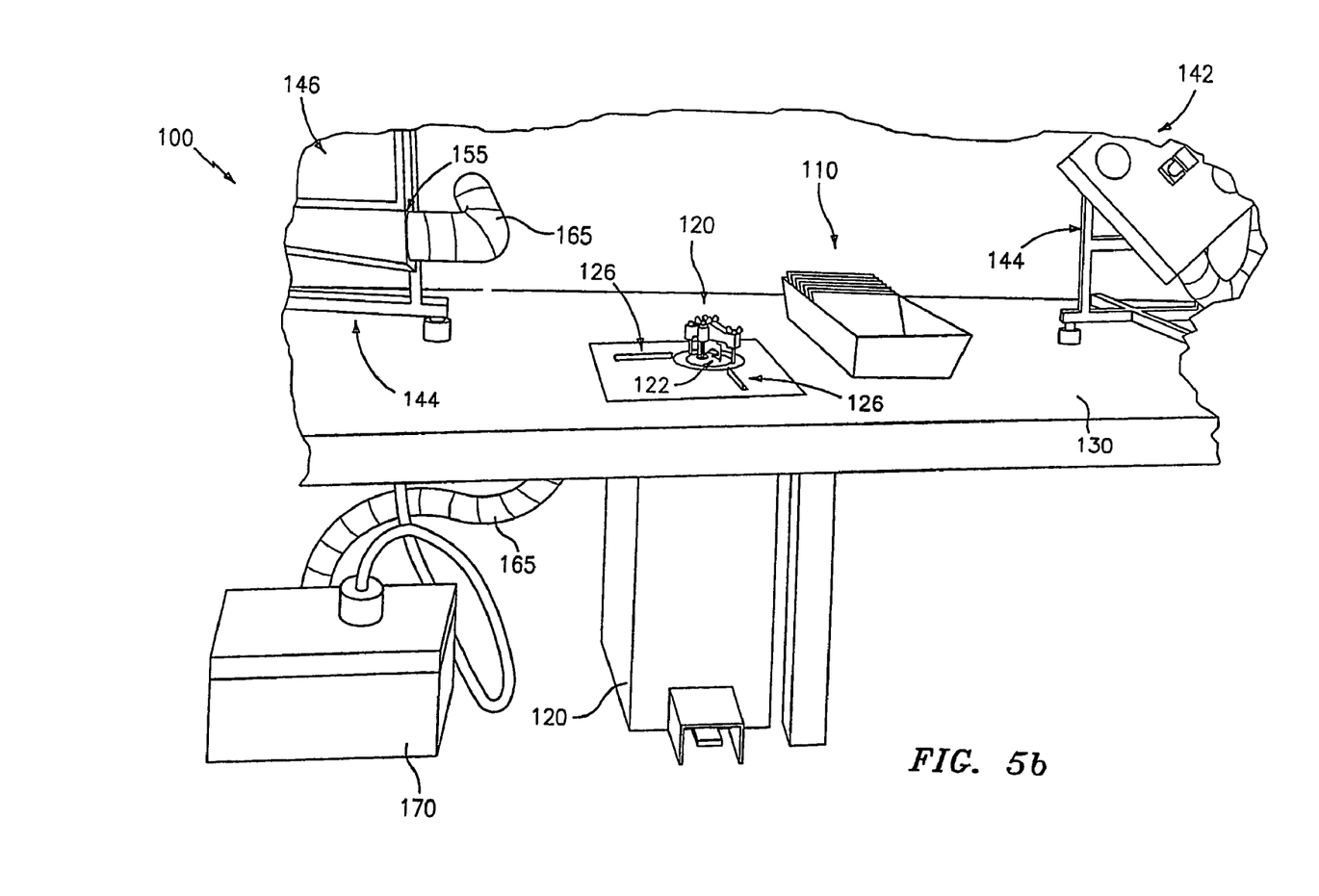

Also shown on FIGS. 2, 5a and 5b is a translucent hood 180 that protects the operator and other personnel from inadvertent contamination by contaminants released by the cutter 120 or the jogger(s). FIG. 5a also shows a manifold 195 that is utilized to connect the apparatus 100 to an external air filtration system that preferably places the apparatus 100 under a slight negative atmospheric pressure, thereby pulling the contaminants away from the operator. Preferably, for the embodiment shown in FIGS. 5a and 5b, each particulate concentrator 190 draws approximately 27 cfm (cubic feet per minute) and the manifold 195 draws between approximately 1,100 and 1,500 cfm.

Figure 6A:
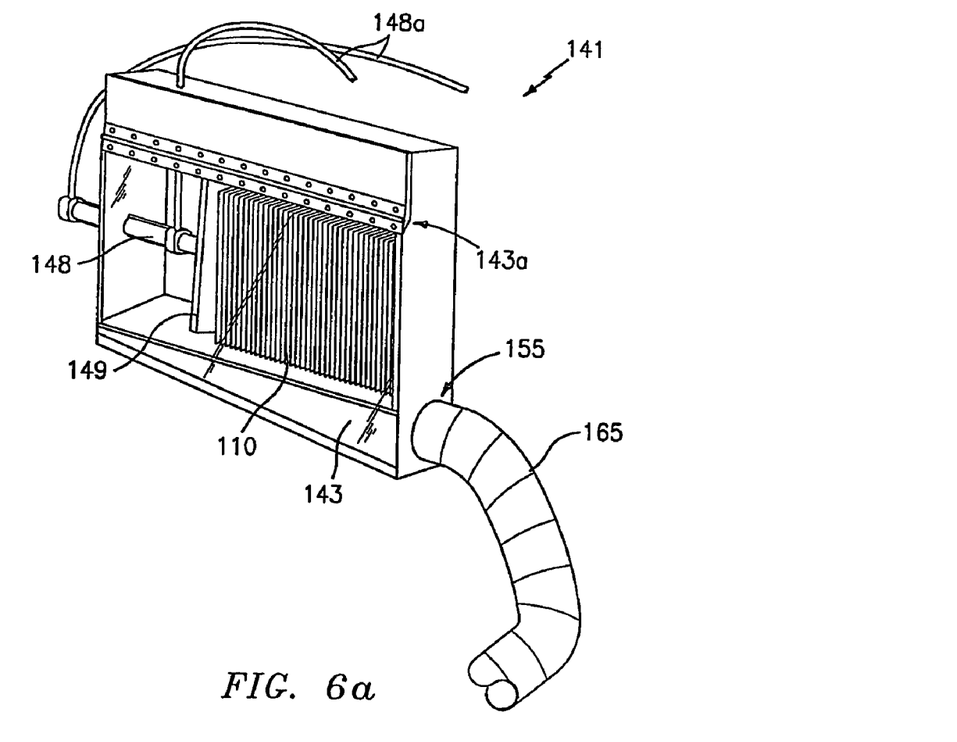
FIG. 6a is a perspective view of a first class mail jogger used in the apparatus.
Figure 6B:
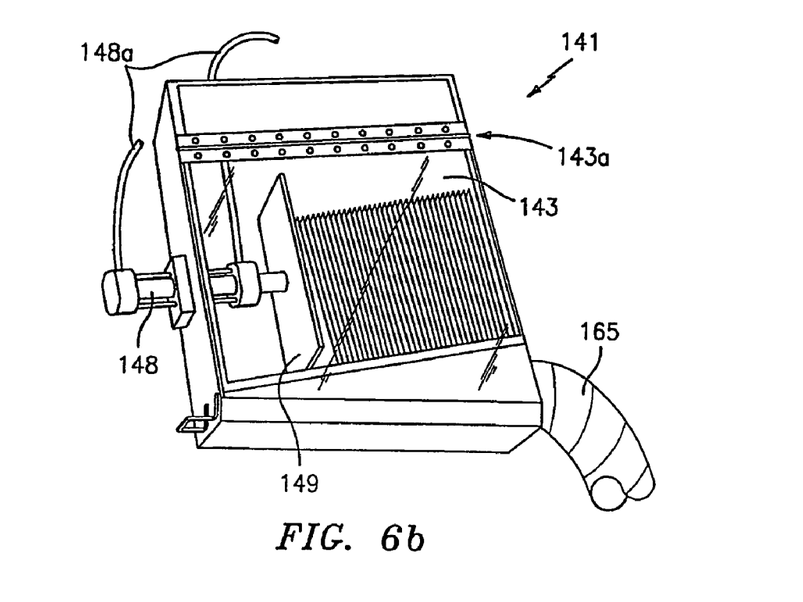

The first class mail jogger 146 shown in FIG. 4a is shown in further detail in FIGS. 6a and 6b.

The first class mail jogger 146 is constructed to accommodate a plurality of similarly sized parcels 110, typically folded first class mail in standard size business envelops juxtaposed positioned in the bin 141. The ram 148 of the first class jogger 146 travels in a longitudinal direction, applying compressive force toward the port 155.

The flats jogger 142 more readily accommodates flat parcels 110. In contrast to the sideward stroke of the ram 148 of the first class mail jogger 146, the ram 148 of the flats jogger 142 has a front to back stroke, moving toward the rear of the apparatus 100. It was found to be preferable to extract the air flow 160 from the flats jogger 142 at a slightly higher velocity than from the first class mail jogger 146.

Although the preferred embodiments include a cutter 120 for initially creating an opening in each parcel 110, it has been observed that the present invention be utilized to screen parcels without the cutter 120.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for rapid screening of parcels to identify parcels likely to contain particles of biological or non-biological contaminants, comprising the steps of:
   opening each parcel;
   shaking the parcels;
   creating an air flow over the parcels as the parcels are shaken;
   sampling particles in the air flow to detect whether the parcels are likely to include contaminants;
   collecting particles in the air flow with a particulate concentrator equipped with a filter; and analyzing the filter periodically to provide a second-check of the accuracy of the sampling step;

wherein the filter is provided with a unique identifier corresponding to a group of parcels found to be non-suspect during the sampling step thereby permitting the non-suspect group of parcels to be identified and re-screened if particles of biological or non-biological contaminants are detected during the analyzing the filter step.

2. The method of claim 1, the sampling step comprising the step of utilizing predetermined characteristic signatures of particles.

3. The method of claim 2, the utilizing predetermined characteristic signatures of particles step comprising at least one of a threshold detection and a Multivariate Gaussian classifier.

* * * * *